United States Patent [19]

Vestal

[11] Patent Number: 4,958,529

[45] Date of Patent: * Sep. 25, 1990

[54] INTERFACE FOR COUPLING LIQUID CHROMATOGRAPHY TO SOLID OR GAS PHASE DETECTORS

[75] Inventor: Marvin L. Vestal, Houston, Tex.

[73] Assignee: Vestec Corporation, Houston, Tex.

[*] Notice: The portion of the term of this patent subsequent to Nov. 28, 2006 has been disclaimed.

[21] Appl. No.: 440,230

[22] Filed: Nov. 22, 1989

[51] Int. Cl.$^5$ ............................................. G01N 1/00
[52] U.S. Cl. ................................. 73/864.81; 250/288
[58] Field of Search .............. 73/863, 863.01, 863.02, 73/863.11, 863.12, 863.21, 864.81, 864.85; 250/281, 282, 288, 288 A

[56] References Cited

U.S. PATENT DOCUMENTS 4,112,297  9/1978  Miyagi et al. .................... 250/281
4,730,111  3/1988  Vestal ............................... 250/288

OTHER PUBLICATIONS

"Combined Supercritical Fluid Chromatography/Mass Spectrometry (SFC/MS)", Arpino, pp. 1170–1186.
"Supercritical Fluid Chromatography–Mass Spectrometry: A Complementary Technique to GC–MS and LC–MS", Chapman et al, pp. 1188–1189.
"Studies with Packed and Capillary Column Supercritical Fluid Chromatography/Mass Spectrometry", Games et al, pp. 1190–1191.
"Detection of Aerosol Formation in the Effluent of a Supercritical Fluid Chromatography", Goates et al, Analytical Chemistry, vol. 59, No. 24, 12/15/87, pp. 2927–2930.

Primary Examiner—Robert Raevis
Attorney, Agent, or Firm—Browning, Bushman, Anderson & Brookhart

[57] ABSTRACT

An improved interface is provided for receiving effluent from a chromatographic device and outputting sample particles of interest to a detector for analysis. The interface includes a gas diffusion cell having a membrane therein separating the cell into an aerosol flow chamber and a sweep gas flow chamber. The effluent is sprayed as an aerosol into the aerosol flow chamber, and vaporized solvent diffuses through the gas membrane into the sweep gas flow chamber while particles of interest are output to the detector. Sweep gas is passed through the sweep gas flow chamber for removing the solvent vapor, and the flow rate of sweep gas is controlled to achieve little or no net flow of gas across the membrane. Efficient solvent removal may be achieved at room temperature for certain LC flow rates, and high detector resolution is possible by maintaining laminar flow of the carrier gas through the aerosol flow chamber.

31 Claims, 2 Drawing Sheets

INTERFACE FOR COUPLING LIQUID CHROMATOGRAPHY TO SOLID OR GAS PHASE DETECTORS

This case is a continuation of Ser. No. 285,516 filed on 12.16.88 and now U.S. Pat. No. 4,883,958.

BACKGROUND OF THE INVENTION

1. Field of the Invention

The present invention relates to devices which interface between liquid or supercritical fluid chromatographic units and gas phase or solid phase detectors and, more particularly, relates to an improved interface which transports the sample as an aerosol while efficiently removing most of the solvent vapors.

2. Description of the Prior Art

The detection of effluent from chromatographic devices has been applied to almost all areas of science requiring chemical analysis. Such detectors usually involve the measurement of either (1) a bulk property of the effluent (such as the refractive index) which is sensitive to the presence of the sample, (2) a property of the sample not possessed by the mobile phase (such as optical density at a suitable wavelength), or (3) a property of the sample after elimination of the mobile phase.

In liquid chromatography (LC), the properties of the sample in the mobile phases are often similar to those of the mobile phase itself. An almost universal LC detector comparable to flame ionization for gas chromotography (GC) does not currently exist. Accordingly, reliable detection of LC samples has generally been obtained using equipment specially designed for limited purposes. While LC is applicable to a much broader range of samples than GC, its limited utility is thus partially attributable to the lack of a suitable universal LC detector.

Packed and capillary supercritical fluid chromatography (SFC) are complementary to GC and LC for the analysis of organic compounds. Packed column SFC allows faster analysis and method development, whereas capillary SFC provides better chromatographic efficiency and allows the use of GC detectors. SFC typically uses a relatively nonpolar gas, such as carbon dioxide operated at a high pressure above the critical point. The addition of more polar modifiers, such as methanol, allows SFC to be applied to a wide range of compounds not amenable to GC. When capillary columns are used with pure carbon dioxide as the mobile phase, SFC can be directly coupled to GC detectors with little difficulty. However at the higher flow rates used with packed columns and the addition of polar modifiers, the same kinds of problems common to an LC interface are encountered in coupling SFC to gas phase detectors.

The thermospray technique was developed primarily for coupling liquid chromatography to a particular gas phase detector, namely mass spectrometry. Thermospray technology provides an LC to mass spectrometry interface which has significant advantages compared to other coupling techniques. In thermospray technology, the LC effluent is partially vaporized and nebulized in a heated vaporizer probe to produce a supersonic jet of vapor containing a mist of fine droplets or particles. As the droplets or particles travel at a high velocity through the heated ion source, they continue to vaporize due to rapid heat input from the surrounding hot vapor. Thermospray thus employs controlled heating of the capillary and the ion source to convert the LC liquid stream into gas phase ions for introduction into the mass spectrometer. A more detailed description of the major components and function of the thermospray system are disclosed in U.S. Pat. No. 4,730,111.

A significant disadvantage of thermospray, as well as other direct coupling techniques between liquid chromatographic devices and mass spectrometers, is that ionization occurs in a bath of solvent vapor at a relatively high source pressure (typically 1 torr or more). This pressure effectively precludes the use of electron impact (EI) ionization, and also limits the choice of reagents in chemical ionization (CI). Moreover, detection utilizing thermospray interface technology has heretofore been limited to a fairly narrow range of chromatographic conditions, since thermospray ionization performs best when the solvent flow rate is in excess of 1 mL/minute, and at least 20% of the mobile phase is water.

Various attempts have been made to overcome the limitations of interfaoes between liquid chromatographic units and detectors. One commercially successful technique is similar to that described in U.S. Pat. No. 4,055,987. This technique unfortunately involves various moving wires and belts, and accordingly has significant operational drawbacks which have become widely recognized by those skilled in the art.

A second type of liquid chromatography to gas phase detector interface is known by the acronym MAGIC, which stands for Monodisperse Aerosol Generation Interface for Chromatography. In this device, the LC effluent is forced under pressure through a relatively small orifice (typically 5 to 10 microns in diameter, such that the liquid jet breaks up into a stream of relatively uniform droplets as a result of Rayleigh instability. A short distance downstream, the stream of particles is intersected at 90° by a high velocity gas stream (usually helium) to disperse the particles and prevent coagulation. The dispersed droplets proceed at a relatively high velocity through a desolvation chamber, where vaporization occurs at atmospheric pressure and near ambient temperature. Heating is input to the desolvation chamber to replace the latent heat of vaporization necessary for solvent evaporation, while not raising the aerosol temperature above ambient. Ideally all the solvent is vaporized, and the sample remains as a solid particle or a less volatile liquid droplet. Further details regarding the MAGIC approach are disclosed in an article by Willoughby and Browner published in 1984 in ANALYTICAL CHEMISTRY, Vol. 56, commencing at page 2626, and in U.S. Pat. No. 4,629,478.

A modified version of a particle beam interface between liquid chromatography and mass spectrometry is disclosed in a series of recently published articles. This technique, referred to as Thermabeam LC/MS, uses a nebulizer which may be similar to a thermospray vaporizer. The interface includes a nebulization stage, an expansion stage, and a momentum separation stage, each axially connected in series. In both the MAGIC and the Thermabeam LC/MS devices, some of the carrier gas and some of the solvent vapor is removed in the momentum separator, but no carrier gas or solvent vapor is removed from the desolvation chamber.

While both the second and third types of interfaces described above apparently produce EI spectra in good agreement with library spectra using sample injections of 100 ng or more, these spectra do not include the low mass region where solvent interference may be expected. Accordingly, it is difficult to determine or evaluate the solvent removal efficiency actually achieved by these techniques. Moreover, improved techniques are required to improve sensitivity for gas phase detectors supplied with effluent from LC and HPLC equipment, and to enable the detectors to be utilized over a broader range of chromatographic conditions. Finally, an improved interface is required which will allow LC effluent to be transmitted for analysis to various types of gas phase detectors, so that the flexibility and versatility of the interface is enhanced and its costs minimized.

The disadvantages of the prior art are overcome by the present invention, and improved methods and apparatus are hereinafter disclosed which provide an interface for coupling liquid chromatography or supercritical fluid chromatography to various types of gas phase detectors.

SUMMARY OF THE INVENTION

The interface of the present invention may be used with various types of gas phase and solid phase detectors, and provides a substantially universal solution to detection of LC effluent. The LC solvent is vaporized and the solvent vapor is efficiently removed, and substantially all samples (except perhaps the most volatile) may be transferred as a particle beam and merged with a carrier gas selected for the particular detector. Pyrolysis and other uncontrolled chemical modifications of the sample may be precluded during this process, and thus thermally labile and nonvolatile components may be readily analyzed by an appropriate detector. The techniques of the present invention are applicable to a wide range of LC flow rates, and essentially all LC mobile phases (even those containing nonvolatile buffers) may be used with the interface of the present invention provided that the introduction of the nonvolatile material can be accommodated by the particular gas phase detector employed.

In a suitable embodiment of the present invention, the interface includes a nebulizer which discharges a high velocity vaporized solvent (wet) jet carrying an aerosol of particles of interest directly into a solvent removal chamber. The solvent removal device includes an interior particle flow chamber and an exterior sweep gas chamber, and the two chambers are separated by a gas diffusion membrane. Sprayed particles from the nebulizer are input at one end into the particle flow chamber with a carrier gas. A sweep gas is input and removed from the sweep gas chamber in a counterflow direction. Solvent vapor in the particle flow chamber passes through the membrane, and is removed by the sweep gas. Most if not substantially all of the solvent vapor is removed, and a resulting dry aerosol may then be transmitted to a suitable detector, either directly or through a particle beam momentum separator to increase the concentration of particles relative to the remaining solvent vapor and carrier gas.

The flow path through the particle flow chamber preferably has a substantially uniform cross-sectional area, such that rapid expansion or contraction of the fluid stream is minimized, and "dead spaces" are eliminated. A series of such chambers may be provided, with each chamber removing a portion of the solvent vapor. The solvent is preferably removed from the aerosol of unvaporized sample particles and inert carrier gas in a counterflow process, thereby enabling continuous operation of the system from the LC to the gas phase detectors. Since the interface allows most of the solvent to be removed while the sample is retained and transmitted as an aerosol, several significant advantages are obtained. When used with a particle beam momentum separator to further reduce the pressure of vapor and carrier gas transmitted along with the particles in the aerosol, the technique of the present invention is particularly well suited for use with both EI (electron impact) and CI (chemical ionization) mass spectrometry. Limitations imposed by the transmission of large amounts of solvent vapor in conventional approaches are obviated by the present invention. Also, significant service problems frequently associated with the vacuum pumps used with particle beam separators or conventional thermospray systems are avoided, since in the present invention the vapor load on the vacuum pumps is substantially reduced.

Many of the problems associated with interfacing SFC to gas phase detectors are not as severe as for an LC to gas detector interface, although removal of carbon dioxide and polar organic modifiers is required for efficient operation of many types of detectors. When a supercritical fluid is expanded through a small nozzle, such as the restrictors used at the end of SFC columns, an aerosol is formed and samples are entrained in the aerosol particles. With SFC, it is thus not necessary to nebulize and vaporize the mobile phase since it is already indistinguishable from a high pressure gas. A more detailed discussion of aerosol formation in the effluent from SFC is contained in an article by Groates et al, Anal. Chem. 59, 2927-2930 (1987).

It is an object of the present invention to provide an improved interface for transmitting samples contained in an LC on SFC effluent to a gas phase or solid phase detector.

It is a further object of the present invention to provide an interface which provides an improved signal to noise ratio output from the detector compared to conventional prior art techniques by substantially reducing the amount of solvent transported to the detector.

It is a feature of the invention that particles of interest are transmitted in an aerosol from a nebulizer to a gas phase or solid phase detector in a manner which removes most of the solvent vapor yet relatively few of the particles of interest.

It is a feature of the present invention to provide an LC to gas phase detector interface which utilizes at least one chamber for removing solvent vapor, with the chamber having a substantial uniform cross-sectional gas flow area.

It is another feature of the present invention that the interface is applicable to thermospray technology, so that the controlled partial vaporization of the liquid in the thermospray capillary may occur, with further vaporization occurring downstream from the capillary.

It is a further feature of the present invention that the interface may include a plurality of solvent removal chambers connected in series for continuously removing solvent vapor from the stream and supplying substantially dry particles to the gas phase detector.

It is an advantage of this invention that ambient room air may be employed in certain cases for at least a portion of the sweep gas used to remove solvent vapor, thus substantially reducing operating costs for the interface.

It is an advantage of the interface according to the present invention that a high degree of desired sample information relative to background solvent information can be attained, so that little or no loss of information occurs as a result of the solvent interference. For example, in EI mass spectrometry, sample molecular ions and fragments may be detected even though the masses may coincide with major ions produced from the solvent vapor.

Another advantage of the invention is that a substantial portion of the solvent vapor in the LC effluent is removed by the interface prior to entering a gas phase detector, such that the service life of pumps intended to maintain a desired system pressure level may be substantially prolonged.

It is another advantage of the present invention that the functional components of the interface of the present invention need not include moving parts, so that service and reliability of the interface is enhanced.

These and further objects, feature, and advantages of the present invention will become apparent from the following detailed description, wherein reference is made to the figures in the accompanying drawings.

DETAILED DESCRIPTION OF PREFERRED EMBODIMENTS

The method and apparatus of the present invention are suitable for coupling LC on SFC effluent to various GC detectors. In some cases, it may be necessary to interpose means for vaporizing the sample particles immediately prior to the detector. For many gas phase detectors, it is not necessary to preserve the molecular integrity of the sample, and various conventional means may be used for vaporizing the particles even if thermal degradation of a sample occurs. Other detectors, such as mass spectrometry and FTIR, provide information regarding molecular weight and/or molecular structure, and accordingly it is essential to avoid pyrolysis or other uncontrolled chemical modification of the sample. Examples of gas phase detectors which may be used with the interface of the present invention are flame ionization detectors (FID), flame photometric detectors (FPD) for specific elements (such as P and S), thermionic ionization detectors (TID), atomic absorption (AA), photoionization, thermal conductivity, mass spectrometry, inductively coupled plasma detectors (ICP), and Fourier transform infra-red (FTIR).

In order to more fully appreciate the features and advantages of the present invention, a background discussion of vaporization and nebulization theory, removal of solvent vapor in a gas diffusion cell, and vaporization of liquid droplets within a gas diffusion cell are provided below.

Vaporization of Liquid Droplets and Small Particles

When liquid is forced at high velocity through an unheated capillary tube, a solid jet issues from the tube, and breaks up into regular droplets according to Rayleigh's theory of liquid jet stabilty. Break up leads to droplets with uniform diameters approximately 2 times the diameter of the nozzle, and a train of droplets of a uniform size and velocity are thus produced. If the tube is heated gently, the properties of the jet are modified slightly by the drop in surface tension accompanying the increase in temperature, although little change is visually observed. When enough heat is applied to produce significant vaporization inside the capillary, the appearance of the jet changes drastically as it is partially vaporized and nebulized into a very large number of small droplets. A further increase in the applied heat reduces the visibility of the jet since the size of the droplets decreases due to further vaporization at high enough heat, and the only visual evidence of the jet is downstream condensation which occurs due to cooling.

A detailed analysis of the process occurring when liquid is vaporized as it is forced through a heated capillary tube is set forth in U.S. Pat. No. 4,730,111 and pending U.S. Application Ser. No. 202,093 filed June 3, 1988, each hereby incorporated herein by reference. For purposes of the present discussion, it should be understood that the rate of vaporization, Z, of a liquid at temperature, T, is given by an equation $$Z = \frac{Pv(T) - Pa}{(2\pi m k T)^{\frac{1}{2}}} \qquad \text{Equation 1}$$

where $Pv(T)$ is the equilibrium vapor pressure at temperature T, Pa is the ambient pressure of the vapor, m is the molecular mass, and k is Boltzmann's constant. The effective vaporization velocity, $V_v$, may be obtained by multiplying by the molecular mass and dividing by the density, $\rho_L$, of the liquid, such that $$V_v = \frac{Pv(T) - Pa}{\rho L} \left( \frac{m}{2\pi k T} \right)^{\frac{1}{2}} \qquad \text{Equation 2}$$

The thermospray vaporizer shares many of the properties of a concentric pneumatic nebulizer used in atomic spectroscopy, in that a high velocity gas is used to shatter a liquid stream into a fine jet of droplets swept along in a gaseous stream. A significant feature of thermospray is that the nebulizing gas is generated in situ by partial vaporization of the liquid. Various attempts have been made to directly measure the droplet size distribution produced by thermospray, but these efforts have met with limited success primarily because a very large number of small, high velocity droplets are produced.

The total number of droplets produoed per second $N_d$ may be determined by the volume of the unvaporized liquid divided by the average volume of the droplets at the instant of nebulization from the bulk liquid. This relationship may be expressed as $$N_d = \frac{10^{11}}{\pi} \left( \frac{F(1 - f)}{d^3} \right) \qquad \text{Equation 3}$$

where F is the liquid flow rate expressed in mL/min., f is the fraction vaporized, and d is the droplet diameter in microns.

The rate of vaporization of a spherical liquid droplet, in turn, can be expressed by the equation $$\frac{dr}{dt} = -V_v \qquad \text{Equation 4}$$

where r is the radius of the droplet, and $V_v$ is the net vaporization velocity calculated according to Equation 2. Since this rate is independent of r, the isothermal lifetime of a droplet can be expressed as a function of vaporization velocity. For water particles at 200° C. in the presence of water vapor at one atmosphere, the net velocity of vaporization is about 100 cm/sec. The isothermal lifetime of water droplets under these conditions is about 1 microsecond per micron radius. At 100° C., water droplets and its vapor at one atmosphere are in equilibrium, and the net rate of vaporization is zero. The very strong dependence of vaporization rates on temperature thus implies that the thermal environment of the droplet particles must be properly controlled for efficient vaporization and ion production.

It should be noted that the above analysis contains several unstated approximations and assumptions, which are probably not strictly valid. For example, it is assumed throughout that a single temperature characterizes the walls of the vaporizer, the vapor, and the liquid at any point along the vaporizer. Since heat is conducted from the walls of the vaporizer through the vapor to the liquid droplets, it is apparent that significant temperature differences must be involved.

If the initial droplet diameter and its thermal history were precisely known, then the droplet vaporization lifetime could be accurately calculated. In the absence of such detailed information, the parameters can be adjusted emperically to achieve complete vaporization of the solvent in the droplets at the exit from the desolvation chamber of the interface. The parameters which affect the droplet lifetime within the interface of the invention are accordingly the thermospray vaporization parameters, namely the temperature of the jetstream from the vaporizer, the diameter of the droplets, and the temperature and pressure of the carrier gas, which then determines the heat transfer to the droplets. If the sample is expected to contain components only slightly less volatile than the solvent, it may be necessary to carefully adjust thermospray conditions for the interface to achieve satisfactory transmission of volatile sample components while simultaneously efficiently removing the solvent.

Vaporization of sample particles is governed by the same equation as those given for liquid droplets, but since sample concentration is normally small compared to the solvent, the ambient partial pressure of sample vapor is negligibly small. As a result, the lifetime of small sample particles may be quite short even though the sample vapor pressure may be several orders of magnitude smaller than that of the solvent. Assuming a spherical droplet dries to yield a spherical dry particle containing the relatively less volatile solute, then the diameter of the final dry particle relative to that of the initial liquid droplet is given by $$d_f = d_o C^{\frac{1}{3}} \left(\frac{\rho L}{\rho S}\right)^{\frac{1}{3}} \qquad \text{Equation 5}$$

where $\rho_S$ is the density of the dry sample, $\rho_L$ is the density of the liquid droplet, and C is the sample concentration (g/g) in the liquid at the point of nebulization. Thus, if the initial droplet diameter is ca. 10 microns, then a sample concentration of 1 part per thousand will yield dry particles of 1 micron diameter, while a sample concentration of 1 part per billion will produce 0.01 micron particles.

Figure 1:
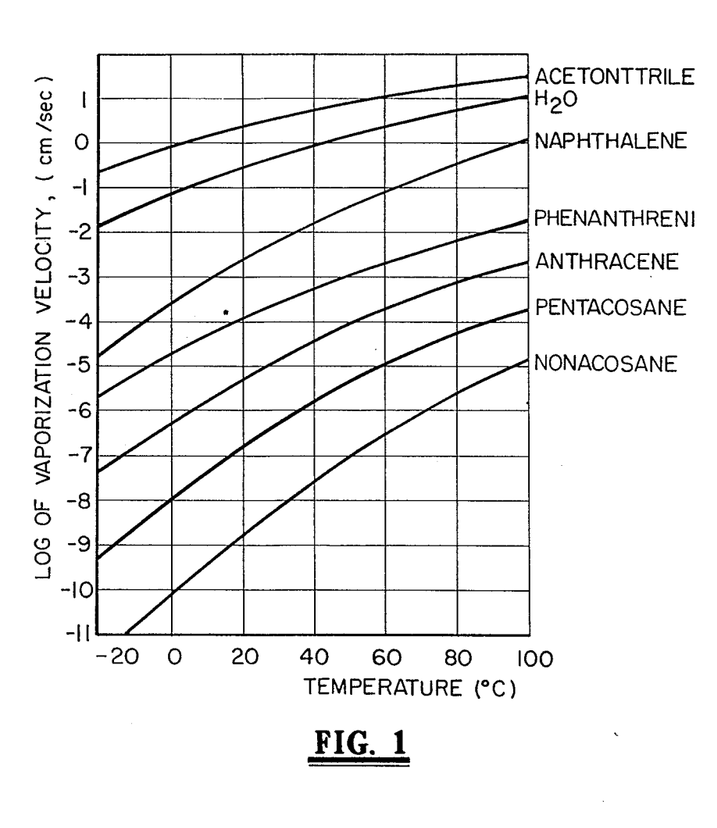
FIG. 1 graphically depicts vaporization velocities as a function of temperature for various substances calculated in accordance with the concepts of the present invention.

The dependence of vapor pressure on temperature for common LC solvents, such as water and acetonitrile, for many relatively volatile solid samples, such as naphthalene, phenarthrene and anthracene, and for less volatile materials, such as pentacosane and nonacosane, is well documented. Vaporization velocities for these substances calculated according to Equation 2 are shown in FIG. 1 for the case in which the ambient pressure of the vapor of the compound in question is negligible. For one such compound, anthracene, the vaporization velocity is approximately $10^{-5}$ cm/sec at room temperature (25° C.), increases to ca. $10^{-4}$ cm/sec at 55° C., and decreases to about $5 \times 10^{-8}$ cm/sec at $-20°$ C. Thus the lifetime of an anthracence particle 2 microns in diameter is about 10 seconds at room temperature and only 1 second at 55° C. Since the transit time through the interface is typically on the order of ten seconds, one could expect to transport some of the anthracene without vaporization at room temperature, but almost none at 55° C. At lower concentrations of anthracene which correspond to smaller particles, this loss should become more severe even at room temperature. On the other hand, at $-20°$ C. vaporization of anthracene should be negligible even for particles as small as 0.01 micron in diameter. The very steep dependence of vapor pressure on temperature implies that modest temperature reductions oan provide large improvements in sample transmission for even slightly volatile compounds.

Removal of Solvent Vapor from the Carrier Gas Chamber

Figure 2:
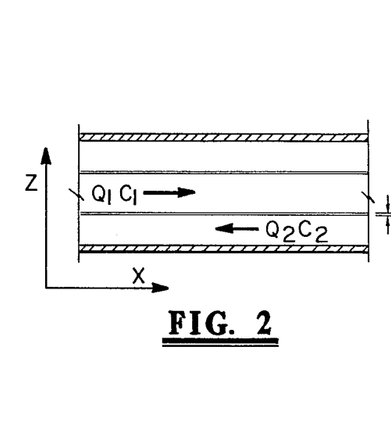
FIG. 2 illustrates a simplified portion of a gas diffusion cell useful for the removal of solvent vapor from the particles of interest.

The mechanism for removal of solvent vapor from the carrier gas chamber can be understood in more detail by reference to FIG. 2, which shows a small section of a solvent removal device (sometimes referenced to as a cell). The total flow in the carrier gas chamber is $Q_1$ (cm$^3$/sec) containing a concentration $C_1$ of vapor, and $Q_2$ and $C_2$ are the corresponding quantities for the sweep gas chamber. The thickness of the filter medium is dz (cm), w is the width of the chamber in the direction perpendicular to the figure, L is the length of the solvent removal device in the direction of the flow, and D is the vapor diffusion coefficient through the filter. If there is no net gas flow across the filter, then the flows $Q_1$ and $Q_2$ are constants set by the gas supply means, and are independent of the vapor concentration at each point in the device. If one assumes that diffusion within the chambers is rapid compared to diffusion through the filter, then the concentration of vapor in each chamber is essentially uniform across each channel at a particular location x, and solvent removal is determined entirely by diffusion of vapor across the filter. These simplifying assumptions reduce the relatively complex three dimensional diffusion problem to a pseudo one dimensional problem.

Fick's law of diffusion (in one dimension) combined with conservation of mass gives $$Q_1 \left( \frac{dC_1}{dx} \right) dx = \frac{-Dwdx}{dz} (C_1 - C_2) = -(-Q_2) \left( \frac{dC_2}{dx} \right) dx \quad \text{Equation 6}$$

The boundary conditions which must be satisfied are $C_1 = C_o$ at $x=0$, and $C_2=0$ at $x=L$. The initial concentration of vapor $C_o$ is given by $C_o = Q_v/Q_1$, where $Q_v$ is the flow rate of input vapor produced by vaporizing the supplied liquid.

The solvent removal factor (efficiency) is then the ratio of the initial concentration of vapor $C_o$ to that at the exit from the carrier gas chamber, $C_1(L)$. The general solution to this problem is given by $$\frac{C_o}{C_1(L)} = \left[ 1 + \frac{Q_1}{Q_2 - Q_1} (1 - e^{-\alpha L}) \right] e^{\alpha L} \quad \text{Equation 7}$$

where $$\delta = \frac{Dw}{Q_1 dz} \left[ 1 - \frac{Q_1}{Q_2} \right]$$

This rather complicated result can be reduced to somewhat simpler expressions for several limiting cases of interest. The one of most practical interest is that corresponding to the sweep gas flow $Q_2$ being much larger than the carrier flow, $Q_1$. This corresponds to $\alpha_L$ much greater than unity, in which case efficient solvent removal can be realized. In this case the solvent removal factor is given by the simple exponential factor $$\frac{C_o}{C_1(L)} = e^{\alpha L} \quad \text{Equation 8}$$

The other extreme occurs for $Q_2$ much less than $Q_1$. In this case the solvent removal factor reduces to $$\frac{C_o}{C_1(L)} = 1 + \frac{DwL}{Q_2 dz} /(1 - \alpha) \quad \text{Equation 9}$$

which approaches unity (i.e. no solvent removal) as the sweep gas flow approaches zero. Another case of some interest is that corresponding to $Q_1 = Q_2$. In this case the solvent removal factor is given by $$\frac{C_o}{C_1(L)} = 1 + \frac{DwL}{Q_2 dz} \quad \text{Equation 10}$$

The only parameters appearing in the above treatment which are not immediately available are the diffusion coefficient D and the membrane thickness dz. Under the simplified treatment used, these correspond to the effective value of the vapor diffusion coefficient through the membrane and the membrane thickness itself. Although the above treatment is not expected to be precisely valid, the effective value of the ratio D/dz can be practically determined for a particular solvent removal device by measuring the solvent removal factor at particular values of $Q_1$ and $Q_2$ such as the case $Q_1 = Q_2$. The solvent removal factor expected for any other value of the flows or different overall lengths L can then be calculated and the system can be set up to achieve any desired degree of solvent removal.

Vaporization of Liquid Droplets within the Carrier Gas Chamber Cell

Figure 3:
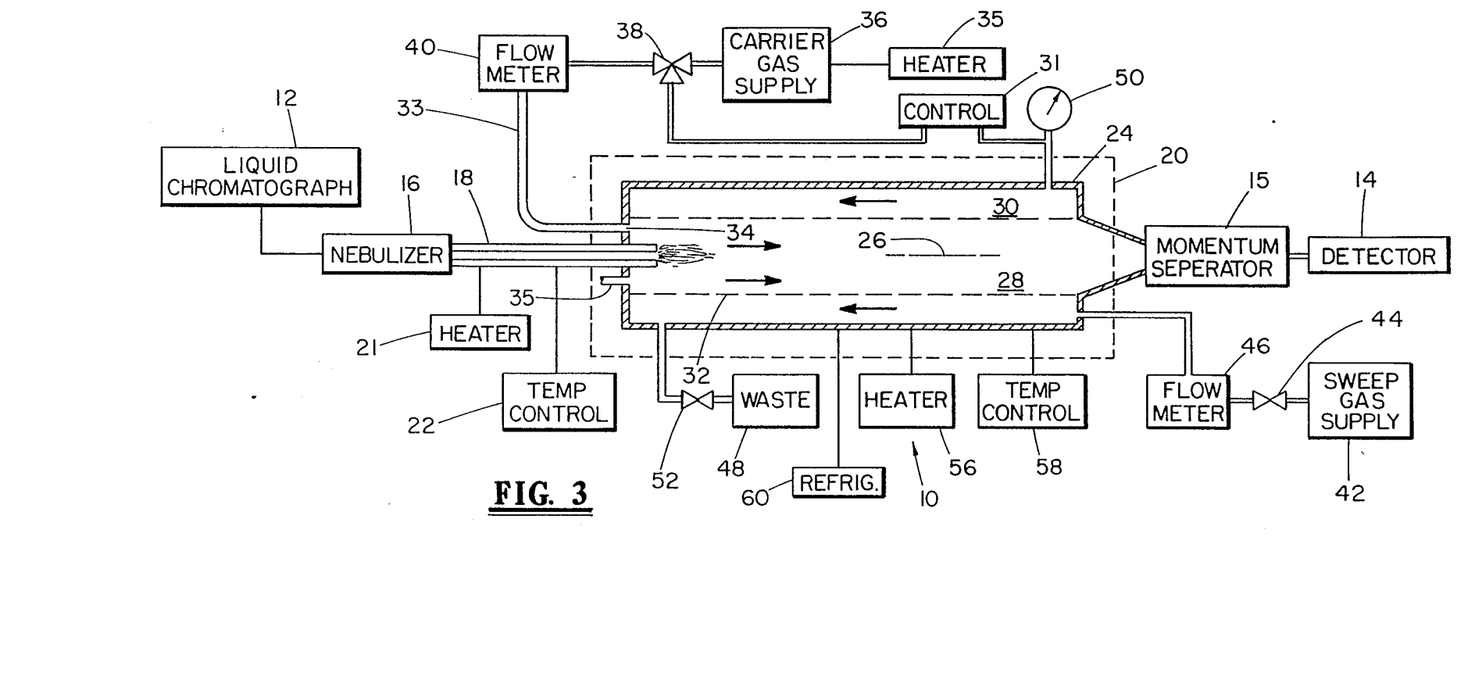
FIG. 3 is a combination block diagram and simplified pictorial illustration of an interface according to the present invention between a liquid chromatograph device and a gas phase detector.
Figure 4:
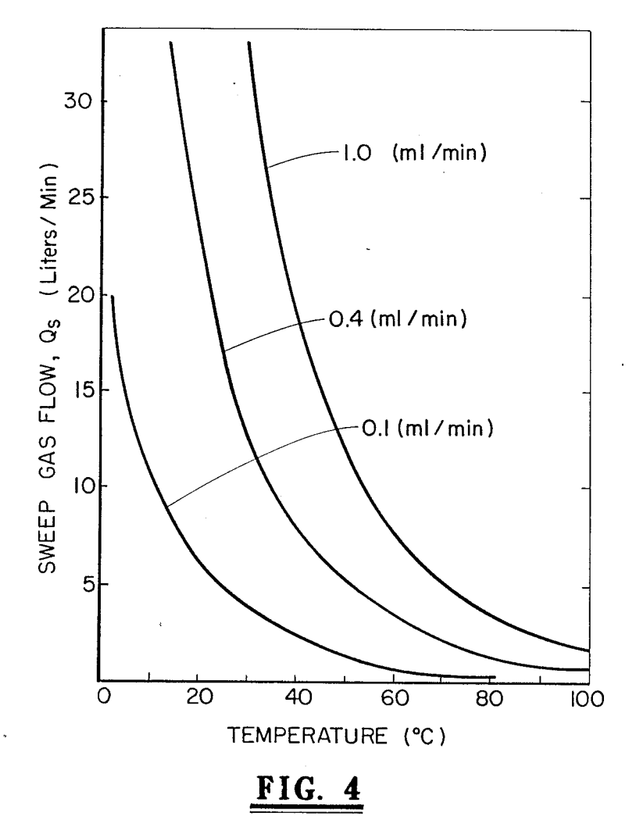
FIG. 4 graphically depicts sweep gas flow rate as a function of temperature required for complete vaporization of various liquids at different flow rates.

In the above treatment, it is assumed that all of the liquid has been evaporated before it reaches the carrier gas chamber. However, it is desirable according to the present invention to vaporize the liquid droplets within the carrier gas chamber to allow vaporization to occur at the minimum possible temperature and without loss of sample to the walls. As long as liquid is present in the chamber (usually in the form of aerosol droplets) the concentration of vapor is given by $$C_1(x) = \frac{P_v(T)}{P} \quad \text{Equation 11}$$

where $P_v(T)$ is the vapor pressure of the liquid and P is the total pressure. The maximum concentration of vapor at the exit of the sweep gas chamber is also given by Equation 10, since when this level is reached no further vaporization occurs. Since $C_1$ is constant at this value throughout the region in which vaporization occurs, the diffusion Equation 5 reduces to $$Q_2 \frac{DC_2}{dx} = -\frac{Dw}{dz} [C_1 - C_2(x)] \quad \text{Equation 12}$$

and the boundary conditions are $C_2(L)=0$, and $C_1(0) \geq C_2(0)$. The expression given in Equation 12 corresponds to flux of vapor from the carrier chamber to the sweep chamber, which in turn must correspond to the rate of vapor production from the liquid droplets. Solving for the vapor concentration in the sweep gas gives $$C_2(x) = C_1[1 - e^{-2'(L-x)}] \quad \text{Equation 13}$$

where $$\alpha^1 = \frac{Dw}{Q_2 dz}$$

and L is the length of the diffusion cell. This result is valid provided the sweep flow, $Q_2$, is sufficiently large that the vapor concentration in the sweep gas at the exit of the sweep gas chamber, $C_2(0)$ is less than $C_1$. This requires that $$Q_2 \geq \frac{RQ_L}{C_1} \quad \text{Equation 14}$$

where R is vapor volume at temperature T divided by the corresponding liquid volume, and $Q_L$ is the liquid input flow rate. Vaporization is complete when the total flux of vapor across the filter is equal to that corresponding to complete vaporization of the liquid. This is expressed by $$\text{FLUX OUT} = \frac{Dw}{dz} \int_0^{L_1} [C_1 - C_2(x)] dx = RQ_L \quad \text{Equation 15}$$

Where $L_1$ is the length of cell required for complete vaporization of the liquid. Carrying out the integration and solving for this distance yields $$L_1 = L - \frac{1}{\alpha^1}\left[\ln\left(\frac{Q_2C_1}{RQ_L}\right)\right] \quad \text{Equation 16}$$

Thus if the sweep gas flow is greater than the minimum value, complete vaporization of the liquid occurs in the first portion of the solvent removal device as given by Equation 16 and solvent vapor removal occurs in the remainder of the device as given by Equation 8, but with L replaced by L-$L_1$. The temperature at which vaporization occurs is governed by the rate of heat transfer to the liquid droplets, but if sufficient sweep gas flow is provided, this vaporization and solvent removal can be done at any desired temperature.

LC to Detector Interfaces

A suitable interface 10 for oaupling the output of a liquid chromatograph 12 to a gas phase detector 14 is shown in FIG. 3. The effluent from the chromatograph is converted to an aerosol by the nebulizer 16, which may be a standard gas flow nebulizer wherein the effluent is not heated and the solvent thus not partially vaporized in the nebulizer. Accordingly, effluent may pass through an unheated capillary tube 18 of the nebulizer and be discharged as a spray directly into the gas diffusion device 20. Alternatively, a thermospray vaporizer may be used as the nebulizer, in which ease a temperature controller 22 can be used to regulate the partial vaporization of the solvent in the capillary tube 18.

With SFC, the effluent may be nebulized by merely passing it through the restrictor at the end of the column directly into the gas diffusion device 20.

The gas diffusion device 20 comprises a sleeve-shaped housing 24, which may be conveniently formed about a central axis 26. The housing has an axially aligned effluent input port at one end for receiving flow from the nebulizer, and a similarly aligned aerosol output port at an opposing end for passing the dry aerosol to a momentum separator 15 and then to the detector 14.

The interior of the housing 24 is divided into a radially interior aerosol flow or carrier gas flow chamber 28 formed about axis 26, and an exterior sweep gas flow chamber 30, with the chambers 28 and 30 being separated by a filter membrane 32. The gas diffusion device as shown in FIG. 3 utilizes a sweep gas chamber 30 which radially encloses the chamber 28, thereby maximizing the area of the membrane 32 and thus reducing the necessary axial length of the device 20.

The housing 24 includes a carrier gas input port 34 at the effluent input end, which allows a selected pressurized carrier gas from supply 36 to be input to chamber 28 through conduit 33. The selected carrier gas flow is controlled by metering valve 38, and the flow rate is monitored by meter 40. A plurality of input ports may be provided radially about the tube 18 to obtain uniform carrier gas flow within the chamber 28 at the nozzle end 19 of the capillary tube 18, and a representative second carrier gas flow conduit 35 is shown in FIG. 3 radially opposite port 34 for transmitting carrier gas from supply 36 to chamber 28.

If a gas flow nebulizer is used, all or a substantial portion of the carrier gas may be added through the nebulizer as might occur, for example, using a conventional concentrical flow nebulizer. With SFC, the vapor pressure of the effluent (for example, carbon dioxide) is typically more than one atmosphere at room temperature; thus it is not necessary in this case to add a carrier gas unless the input from the chromatograph is less than that required by the detector.

At the opposing end of the device 20, a sweep gas from supply 42 is similarly metered by valve 44, and is input directly to the chamber 30 to cause a sweep gas flow in chamber 30 which is axially counter in direction to the gas flow in chamber 28. The flow of sweep gas may be similarly monitored by 46, and thus both the carrier gas flow and the sweep gas flow through the device can be easily detected. The sweep gas is output from the effluent input end, and may be dumped to a waste container 48. Sweep gas pressure in chamber 30 is monitored by pressure gauge 50, and sweep gas pressure is controlled by the input metering valve 44 and the output metering valve 52.

A "wet aerosol" mixture consisting of carrier gas, solvent vapor, and sampled particles from the nebulizer 16 passes through the chamber 28 in the gas diffusion device 20, and a "dry aerosol" mixture consisting substantially of carrier gas and sample particles of interest passes from the gas diffusion device to detector 14. The sample particles passing through the device 20 are separated from the solvent vapor by the diffusion membrane 32. The sweep gas, which may be chemically identical to the carrier gas, is introduced into the chamber 30, and flows in the annular chamber 30 between the housing 24 and the membrane 32 in a counterflow direction to the flow of particles through the device 20. The flow rate of the counterflowing sweep gas may be significantly greater than the flow rate of the wet aerosol mixture, and may be two or more times greater, so that at each point along the membrane 32 the concentration of solvent vapor in the oounterflow gas is significantly lower than that in the wet aerosol. The properties of the membrane 32 are not critical, and a variety of filter media have been used successfully. The membrane should be sufficiently permeable that the carrier gas and vapor can diffuse freely across it, yet be a sufficient barrier to flow that any net flow of gas through the membrane is relatively small, and so that no particles of interest pass therethrough. A membrane formed from a fibrous porous form of PTFE has been found to be satisfactory, and such a suitable material is commercially available under the trade name "ZITEX." It should be understood that the membrane 32 may either be tubular in form as described above, or may be provided in a flat sheet. Also, the chambers 28 and 30 need not be aligned with the axis 26 of the housing as shown in FIG. 3, although the aerosol is preferably sprayed along the central axis of the carrier gas chamber.

The interface as shown in FIG. 3 has an advantage over an interface which utilizes refrigerated condensors since no expensive mechanical components, such as refrigerators and pumps, are required. The effective area of the membrane 32 separating the particles in the chamber 28 from the sweep gas in the chamber 30 may be easily controlled to remove the desired amount of solvent vapor. A primary benefit of the membrane-type interface as shown in FIG. 3 compared with the interface utilizing refrigerated condensors relates to the substantial reduction in lost sample particles of interest, particularly for relatively volatile samples in water. A nebulizer of the present invention need not operate at high temperatures required to vaporize less volatile liquids, and accordingly significant vaporization of more volatile sample particles of interest need not occur. Also, the device as shown in FIG. 3 does not rely upon condensation of the solvent vapor to remove the solvent from the particles of interest, and according sample particles of interest are not carried to the condensing walls and lost by redesolving in the condensate. The apparatus as shown in FIG. 3 is thus significantly simplier in design and has a reduced manufacturing cost compared to an interface which utilizes one or more condensors, since a condensor, a drain, and liquid removal pump are not necessary.

Figure 5:
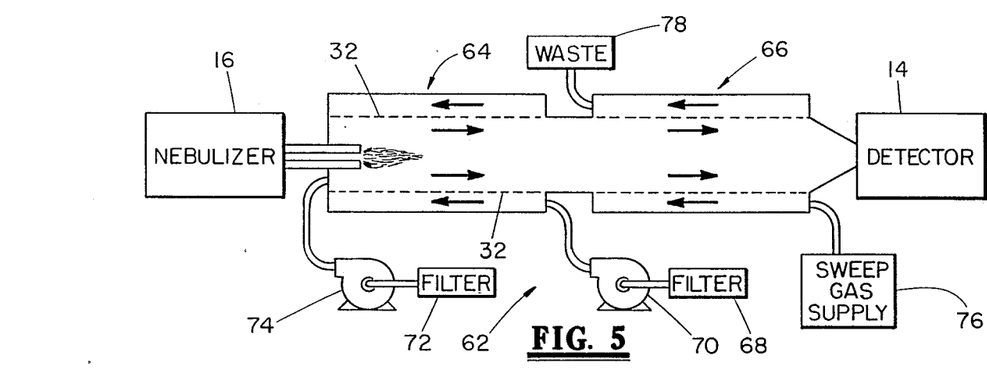
FIG. 5 is a pictorial view of an alternate embodiment of a solvent removal device according to the present invention.

To operate the system as shown in FIG. 3, a nominal value of the flow in the chamber 28 is initially determined by the flow impedance of the gas phase detector 14 or the nozzle in the upstream momentum separator 15. This flow impedance and the pressure in the device 20 measured by gauge 50 determine the total mass flow of dry aerosol and gas to the detector 14. Once the proper mass flow required to give satisfactory detector performance is established, the optimum performanoe of the interface can be adjusted for a particular application to achieve (a) the maximum transmission of sample particles of interest, (b) a minimum effect of solvent flow rate or composition on sample transmission efficiency, (c) removal of the desired amount of solvent, and (d) a minimum consumption of sweep gas.

Sample loss can be minimized by maintaining laminar flow through the chamber 28 and assuring that there is no significant net flow of gas or vapor across the membrane, which reduces the likelihood that sample particles of interest will contact the membrane and become lost. The carrier gas flow should be adjusted to allow the sample to be efficiently transported with a small amount of dispersion in transit time of sample particles. Small transit time dispersion is particularly important for coupling liquid chromatography to detectors, since otherwise the separation of components achieved in the chromatographio columns is degraded before the sample reaches the deteotor. In order to obtain the desired performance of the interface, it thus appears that laminar flow throughout the chamber from the nebulizer to the detector is preferred.

To reduce the likelihood that sample particles may become lost by vaporization, the operating temperature of the aerosol should be kept as low as possible consistant with the concept of vaporizing and removing the solvents. As discussed in the theoretical section above, the ability of the interface according to the present invention to vaporize and remove substantially all solvent is determined by the flow rate of the sweep gas relative to that of the vapor produced by vaporizing the liquid, the dimensions of the unit 20, and the net heat input relative to that required to vaporize the liquid. If the sweep gas flow is very large compared to the total vapor flow, efficient solvent vaporization and vapor removal can be accomplished at temperatures approaching room temperature, while substantially reducing loss of volatile samples due to vaporization. A single stage system as shown in FIG. 3 operating at room temperatures is very economical and convenient for application in which vaporization of the mobile phase is not a significant problem. A single stage, room temperature operating interface will thus be well suited for receiving effluent from a supercritical fluid chromatograph (SFC), from a liquid chromatograph using small columns and low liquid flow rates, or from a liquid chromatograph wherein the samples of interest are dissolved . in predominantly organic mobile phases.

According to the present invention, vaporization is controlled by regulating the temperature of the cell and by regulating the sweep gas flow rate. The flow rate of the carrier gas need not directly influence the vaporization, although the carrier gas flow rate has an influence on the pressure in the aerosol flow chamber and thus the sweep gas flow rate required to obtain the desired balance between the carrier and sweep gas flow rates to prevent significant net gas flow across the membrane. For instances in which an acceptable carrier gas to the detector 14 may be an inexpensive gas, such as air, the techniques of the present invention allow such an inexpensive gas to be used as both the sweep and carrier gas, thereby substantially reducing the cost of operating the interface. The sweep gas flow rates required for complete vaporization of water at specific flow rates from the liquid chromatograph are depicted as a function of the cell temperature in FIG. 4. A flow rate of 0.1 mL/min of water to this interface can be vaporized at room temperature using a sweep flow of only 5 L/min. In order to vaporize a flow rate of 0.4 mL/min. of water at room temperature, the proportionately higher sweep gas flow rate of about 20 L/min is required. As shown in FIG. 4, the required sweep flow is substantially minimized when higher effluent temperatures are utilized.

From the above, it should be understood that the volume of the required sweep gas and the expense of the sweep gas may practically necessitate some sample loss due to vaporization. The temperature of the gas diffusion device 20 and the sweep flow can thus be balanced to allow for complete vaporization and the desired degree of solvent removal, although some loss of the more volatile samples may result from operating the interface such that the effluent in the aerosol flow chamber is at higher temperatures. The temperature within the device 20, in turn, can be controlled by any combination of the heater block 21 thermally in contact with the capillary tube 18 and temperature controller 22 for the nebulizer, heater 35 for the carrier gas supply 36, or heater 56 and temperature controller 58 provided for direct heating of the sweep gas in chamber 30. Heating of the sweep gas may thus be accomplished either before the sweep gas enters the gas diffusion device 20, or by controlling the heating of the housing 24, as shown in FIG. 3. On the other hand, for SFC or LC at low liquid flow rates, the chamber 30 may be lowered to subambient temperatures by refrigerator 60, so that the interface can achieve improved transfer of volatile samples. This latter technique substantially enhances the flexibility of the interface, although it obviously requires increased cost and complexity to achieve the necessary temperature control of the effluent. The minimum sweep gas flow rate required to complete vaporization of the solvent may be determined from Equation 14. To obtain efficient solvent removal, the sweep gas flow will normally be maintained at a level at least twice this minimum flow value.

FIG. 5 depicts a two stage interface system 62 according to the present invention which may be operated at room temperature. In this system, a high flow rate of an inexpensive sweep gas, such as air, is used to vaporize and remove the solvent vapor in a first stage 64 of the system. Laboratory air is thus passed through filter 68 and pressurized by pump 70 for use as the sweep gas in the first stage 64, and a similar filter 72 and pump 74 serve to supply air as the carrier gas in this stage. In many cases, this inexpensive carrier gas is inappropriate as the input to the detector, but this carrier gas may be removed in a second stage 66 using a more expensive carrier gas, such as helium, which is compatible with the detector 14. No additional carrier gas need be added in the second stage 66. Helium, argon, nitrogen, or other sweep gas compatible with the detector 14 is thus input from supply 76, and some of the more expensive sweep gas and the replaced air passing through the membrane 32 in the second stage 66 will flow to waste 78. The system as shown in FIG. 5 allows for a minimum consumption of expensive gas, yet also a minimum loss of volatile samples. In most applications, the two stage system does not require heating, although one or both stages may be cooled to improve the transport of volatile samples.

Although not depicted in FIG. 5, it should be understood that the temperature regulation devices, pressure gauges, and carrier gas and sweep gas controls may be employed for each of the in series gas diffusion devices shown in FIG. 3. To further reduce manufacturing costs, flat sheet filter media may be used. Although the desired axial length of the carrier gas chamber may vary with different applications, a suitable carrier gas chamber may have an axial length of from 2 to 4 meters. In order to reduce the size of the interface, the carrier gas chamber may comprise a plurality of straight portions each interconnected in series by a curved portion. Provided sharp bends in the carrier gas chamber are avoided, such a configuration does not result in any significant loss of sample particles of interest, yet results in a substantially compact interface unit.

From the above, it should be understood that the sweep gas flow and temperature of the effluent may be adjusted to remove the desired quantity of solvent vapor from the effluent. To avoid significant sample losses to the membrane 32, the gas flow may be adjusted as follows. The sweep gas input and exit valves 44 and 52 may first be closed with no liquid flow through the nebulizer, and the carrier gas input valve 38 adjusted to provide a carrier gas flow through meter 40 which is equal to the nominal mass flow to the detector, as explained above. This carrier gas flow practically must be greater than or at least equal to the maximum vapor flow expected from vaporizing the liquid from the nebulizer. Once the carrier gas flow to the detector is so adjusted, the carrier gas pressure within the housing 24 is measured at gauge 50 and recorded. The sweep gas exit valve 52 may then be fully opened, and the sweep gas input valve 44 adjusted to provide the sweep gas flow necessary to achieve the desired degree of solvent removal and the temperature selected to obtain vaporization. Valve 52 may then be throttled back until the pressure previously recorded in housing 24 is again achieved. At this stage, liquid flow through the nebulizer 16 may be commenced, and the carrier gas flow through meter 40 then reduced to return the pressure at gauge 50 to the previous set point. This last correction can be done automatically using a motor controller 31 for valve 30 which is responsive to the pressure sensor 50. In this manner, the interface can be maintained automatically at the optimum flow even though the solvent input composition and flow rate may vary.

During operation of the interface, the gas pressure in the cell housing may be monitored by gauge 50. Any significant change in gas pressure will suggest an interruption of normal gas flow through the interface, and will typically cause the operator to terminate flow through the interface and check gas flow blockage or other malfunction of the interface or detector. The sweep gas flow rate will typically be controlled as a function of the composition and flow rate of the effluent to the interface. The temperature of the cell housing will then be controlled (either by heating the housing to a temperature above ambient or by lowering the cell housing temperature below ambient with refrigeration) to obtain complete vaporization of the solvent, while also maintaining a temperature as low as practical to minimize vaporization of sample particles of interest within the aerosol flow chamber.

Once the sample has reached the specific detector desired, it may be treated as required by the properties of the particular device employed in order to attain maximum detection efficiency for the sample. With gas phase detectors such as PID or FID, the sample particles can be extensively heated in the gas stream or caused to impact on a heated surface, since pyrolysis is not detrimental and only a portion of the sample need be converted to gas so that it may be detected. In other cases, additional conventional elements may be required to complete the coupling between the interface and the particular detector. Those skilled in the art should appreciate that the interface of the present invention can be combined with almost any of the wide range of gas phase and solid phase detectors, so that an essentially "universal" detector between liquid chromatography and gas phase detectors is obtained. Further particulars with respect to a suitable detector are discussed in the parent application, and specific reference is made to FIGS. 6–9 in that parent application for detectors which may be used in accordance with the present invention.

It should also be understood that various nebulizers may be used for discharging the LC effluent spray into the interface. Accordingly, the techniques of the present invention are applicable to thermospray as well as other types of nebulizers, such as variations of the MAGIC or thermabeam concepts discussed earlier.

It should also be understood that a particular solvent may be selected for carrying the samples of interest (solute) through the chromatographic device which will be dependent upon the selected chromatographic unit and the samples to be separated by the process. Preferably, there is a significant disparity between the volatility of the solvent and the volatility of the sample of interest, such that complete vaporization of the solvent occurs within the interface of the present invention without there being a significant vaporization of the samples of interest.

The foregoing disclosure and description of the invention is illustrative and explanatory thereof, and various changes in size, shape and materials as well as the details of the illustrated construction may be made within the scope of the appended claims without departing from the spirit of the invention.

What is claimed is:

1. An improved interface for receiving effluent including sample solute of interest and solvent from a liquid chromatographic device, and for outputting sample particles of interest to a detector for analysis of a sample, the interface comprising:

a gas diffusion device including a cell housing having an aerosol input port and an aerosol discharge port;
spraying means for passing the chromatographic effluent through the aerosol input port and for discharging the chromatographic effluent as an aerosol into the cell housing;

a gas diffusion membrane within the cell housing separating the cell housing into an aerosol flow chamber and an adjoining sweep gas flow chamber, the aerosol flow chamber being in fluid communication with both the aerosol input port and the aerosol discharge port for receiving and transmitting the aerosol to the detector, the sweep gas flow chamber having a sweep gas input port and a sweep gas discharge port for passing sweep gas through the sweep gas chamber in a direction counter to the flow of aerosol through the aerosol flow chamber; and sweep gas supply means for passing a sweep gas through the sweep gas flow chamber while the aerosol is passed through the aerosol flow chamber, such that solvent vapor released from the aerosol discharged by the spraying means is diffused from the aerosol flow chamber through the membrane and to the sweep gas flow chamber, and is removed from the gas diffusion device by the sweep gas.

2. An improved interface as defined in claim 1, further comprising:

a sweep gas inlet valve for controlling the flow of sweep gas to the sweep gas flow chamber.

3. An improved interface as defined in claim 2, further comprising:

a sweep gas outlet valve for controlling the flow of the sweep gas from the flow chamber, such that the sweep gas inlet valve and sweep gas outlet valve control the gas pressure in the cell housing.

4. An improved interface as defined in claim 3, further comprising:

pressure sensing means for determining the gas pressure in the cell housing.

5. An improved interface as defined claim 1, further comprising:

a carrier gas supply means for inputting a carrier gas to the aerosol flow chamber; and a carrier gas inlet valve for controlling the flow of carrier gas to the aerosol flow chamber to substantially equalize pressure across the gas diffusion membrane.

6. An improved interface as defined in claim 5, further comprising:

a sweep gas flow meter for monitoring the flow of sweep gas to the sweep gas chamber; and a carrier gas flow meter for monitoring the flow of carrier gas to the aerosol flow chamber.

7. An improved interface as defined in claim 1, further comprising:

the spraying means including an elongate nebulizer capillary tube for discharging the aerosol into the aerosol flow chamber along substantially a central axis of the aerosol flow chamber.

8. An improved interface as defined in claim 1, further comprising:

temperature sensing means for sensing the temperature of the cell housing; and temperature conditioning means for controlling the temperature of the cell housing.

9. An improved interface as defined in claim 1, further comprising:

a heater for heating the effluent passing through the spraying means prior to being discharged as an aerosol into the cell housing; and thermospray controllor means for regulating thermal output of the heater to vaporize a substantial portion of the solvent from the liquid chromatographic device prior to being discharged into the cell housing.

10. An improved interface as defined in claim 1, wherein the sweep gas is selected from a group consisting of argon, helium and nitrogen.

11. An improved interface as defined in claim 1, wherein the cross-sectional flow area of the aerosol flow chamber in the gas diffusion device remains substantially uniform such that rapid expansion or contraction of the aerosol is minimized.

12. An improved interface as defined in claim 1, further comprising:

a momentum separator between the gas diffusion device and the detector for preferentially removing gas and transmitting the particles of interest to the detector.

13. An improved interface for receiving liquid effluent including sample solute of interest and solvent from a liquid chromatographic device, and for outputting sample particles of interest to a detector for analysis of a sample, the interface comprising:

a gas diffusion device including a first cell housing and a second cell housing in series with the first cell housing;

spraying means for discharging the liquid effluent as an aerosol into the first cell housing;

a first gas diffusion membrane within the first cell housing separating the first cell housing into a first aerosol flow chamber and an adjoining first sweep gas flow chamber;

first sweep gas supply means for passing a first sweep gas through the first sweep gas flow chamber while the aerosol is passed through the first aerosol flow chamber in a direction counter to the flow of the first sweep gas, such that solvent vapor released from the aerosol discharged by the spraying means is diffused from the first aerosol flow chamber through the first membrane and to the first sweep gas flow chamber, and is removed from the gas diffusion device by the first sweep gas;

a second gas diffusion membrane within the second cell housing separating the second cell housing into a second aerosol flow chamber in series communication with the first aerosol flow chamber and an adjoining second sweep gas flow chamber; and second sweep gas supply means for passing a second sweep gas through the second sweep gas flow chamber while the aerosol is passed through the second aerosol flow chamber in a direction counter to the flow of the second sweep gas, such that the first sweep gas in the second aerosol flow chamber is diffused through the second membrane and to the second sweep gas flow chamber, and is removed from the gas diffusion device by the second sweep gas.

14. An improved interfaoe as defined in claim 13, wherein:

the first sweep gas supply means passes air as a selected sweep gas to the first sweep gas flow chamber.

15. An improved interface as defined in claim 14, wherein:

the second sweep gas supply means passes a selected sweep gas through the second sweep gas flow chamber from a group consisting of argon, nitrogen, and helium.

16. An improved interface as defined in claim 13, further comprising:
a second sweep gas inlet valve for controlling the flow of the second sweep gas to the second sweep gas flow chamber; and
a second sweep gas outlet valve for controlling the flow of the second sweep gas from the second sweep gas flow chamber, such that the second sweep gas inlet valve and the second sweep gas outlet valve control gas pressure within the second cell housing.

17. An improved interface method for receiving effluent including sample solute of interest and solvent from a chromatographic device, and for outputting sample particles of interest to a detector for analysis of a sample, the improved interface method comprising:
providing a gas diffusion membrane within a cell housing to separate the cell housing into an aerosol flow chamber and a sweep gas flow chamber;
spraying the effluent as an aerosol into the aerosol flow chamber;
passing a carrier gas through the aerosol flow chamber to carry the aerosol through the aerosol flow chamber and toward the detector;
passing a sweep gas through the sweep gas flow chamber while the aerosol is carried through the aerosol flow chamber in a direction counter to the flow within the aerosol flow chamber;
controlling the sweep gas flow rate to complete vaporization of the solvent from the aerosol within the aerosol flow chamber while diffusing solvent vapor within the aerosol flow chamber through the membrane and into the sweep gas flow chamber;
controlling the carrier gas flow rate within the aerosol flow chamber to substantially equalize pressure across the gas diffusion membrane; and
removing solvent vapor and sweep gas from the cell housing while outputting sample particles of interest to the detector.

18. An improved interface method as defined in claim 17, wherein the step of controlling the carrier gas flow rate includes maintaining laminar flow of carrier gas through the aerosol flow chamber.

19. An improved interface method as defined in claim 17, further comprising:
controlling the sweep gas flow rate through the sweep gas chamber as a function of the composition and flow rate of the liquid effluent; and
regulating the cell housing temperature as a function of the sweep gas flow rate to a level sufficient to obtain complete vaporization of the solvent from the aerosol within the aerosol flow chamber.

20. An improved interface method as defined in claim 19, further comprising:
cooling the cell housing to a subambient temperature to minimize vaporization of sample particles of interest within the aerosol flow chamber.

21. An improved interface method as defined in claim 17, further comprising:
determining the minimum sweep gas flow rate required for complete vaporization of the solvent from the aerosol in the aerosol flow chamber; and
maintaining the sweep gas flow rate at a level at least twice the determined minimum sweep gas flow rate to efficiently remove solvent vapor from the aerosol flow chamber.

22. An improved interface method as defined in claim 17, further comprising:
heating the effluent prior to being sprayed into the aerosol flow chamber.

23. An improved interface method as defined in claim 17, further comprising:
monitoring the pressure in the cell housing, and
controlling operation of the interface in response to the monitored pressure in the cell housing.

24. An improved interface method as defined in claim 17, wherein the selected carrier gas and the selected sweep gas are selected from a group existing of air, nitrogen, argon and helium.

25. An improved interface method as defined in claim 17, further comprising:
spraying the effluent into the aerosol flow chamber in a direction substantially along a central axis of the aerosol flow chamber.

26. An improved interface method as defined in claim 17, further comprising:
(a) determining the desired mass flow rate to the detector;
(b) passing carrier gas through the cell housing at a flow rate substantially equal to the mass flow rate determined in step (a), while no sweep gas or liquid effluent is passed to or from the cell housing;
(c) detecting the carrier gas pressure within the cell housing during step (b);
(d) thereafter passing sweep gas through the cell housing with the carrier gas;
(e) controlling the flow rate of sweep gas through the cell housing during step (d) to produce substantially the pressure within the cell housing detected in step (c);
(f) thereafter commencing the spraying of liquid effluent into the aerosol flow chamber; and
(g) thereafter reducing the carrier gas flow rate through the cell housing to produce substantially the pressure within the cell housing detected in step (c).

27. An improved thermospray interface as defined in claim 26, further comprising:
automatically controlling the carrier gas flow during step (g) in response to detected pressure within the cell housing.

28. An improved interface method for receiving liquid effluent including sample solute of interest and solvent from a liquid chromatographic device, and for outputting samples particles of interest to a detector for analysis of a sample, the improved method comprising:
providing a first gas diffusion cell including a first gas diffusion membrane within a first cell housing to separate the first cell housing into a first aerosol flow chamber and a first sweep gas flow chamber;
providing a second gas diffusion cell including a second gas diffusion membrane within a second cell housing to separate the second cell housing into a second aerosol flow chamber in series with the first aerosol flow chamber and a second sweep gas flow chamber;
spraying the liquid effluent as an aerosol into the first aerosol flow chamber;
passing a carrier gas through the first aerosol flow chamber to carry the aerosol through the first and second gas diffusion cells and toward the detector;
passing a first sweep gas through the first sweep gas flow chamber in a direction counter to the flow of aerosol through the first aerosol flow chamber such that solvent vapor released from the aerosol is diffused from the first aerosol flow chamber through the membrane and to the first sweep gas flow chamber, and is removed from the gas diffusion device by the first sweep gas;

controlling the first sweep gas flow rate through the first sweep gas chamber to complete vaporization of the solvent from the aerosol within the first aerosol flow chamber;

controlling the oarrier gas flow rate to the first aerosol flow chamber to substantially equalize the pressure across the first gas diffusion membrane;

removing solvent vapor and the first sweep gas from the first cell housing while outputting sample particles of interest to the second aerosol flow chamber;

passing a second sweep gas through the second sweep gas chamber in a direction counter to the flow of aerosol through the second aerosol flow chamber such that the solvent vapor, the carrier gas and the first sweep gas are diffused from the second aerosol flow chamber through the second gas diffusion membrane to the second sweep gas flow chamber, and are removed from the gas diffusion device by the second sweep gas; and removing solvent vapor and sweep gas from the second cell housing while outputting sample particles of interest to the detector.

29. An improved interface method as defined in claim 28, further comprising:

controlling the second sweep gas flow rate to a level twice the flow rate through the second aerosol chamber, thereby efficiently removing solvent vapor, carrier gas and first sweep gas from the second aerosol flow chamber and to the detector.

30. An improved interface method for receiving effluent including sample solute of interest and solvent from a chromatographic device, and for outputting sample particles of interest to a detector for analysis of a sample, the improved interface method comprising:

providing a gas diffusion membrane within a cell housing to separate the cell housing into an aerosol flow chamber and a sweep gas flow chamber;

spraying the effluent as an aerosol into the aerosol flow chamber while maintaining the cell housing at ambient temperature;

passing a carrier gas through the aerosol flow chamber to carry the aerosol through the aerosol flow chamber and toward the detector;

passing a sweep gas through the sweep gas flow chamber while the aerosol is carried through the aerosol flow chamber in a direction counter to the flow within the aerosol flow chamber;

controlling the sweep gas flow rate to complete vaporization of the solvent from the aerosol within the aerosol flow chamber while diffusing solvent vapor within the aerosol flow chamber through the membrane and into the sweep gas flow chamber;

controlling the carrier gas flow rate within the aerosol flow chamber to substantially equalize pressure across the gas diffusion membrane and maintain laminar flow of carrier gas through the aerosol flow chamber; and removing solvent vapor and sweep gas from the cell housing while outputting sample particles of interest to the detector.

31. An improved interface method as defined in claim 30, further comprising:

(a) determining the desired mass flow rate to the detector;

(b) passing carrier gas through the cell housing at a flow rate substantially equal to the mass flow rate determined in step (a), while no sweep gas or liquid effluent is passed to or from the cell housing;

(c) detecting the carrier gas pressure within the cell housing during step (b);

(d) thereafter passing sweep gas through the cell housing with the carrier gas;

(e) controlling the flow rate of sweep gas through the cell housing during step (d) to produce substantially the pressure within the cell housing detected in step (c);

(f) thereafter commencing the spraying of liquid effluent into the aerosol flow chamber; and (g) thereafter reducing the carrier gas flow rate through the cell housing to produce substantially the pressure within the oell housing detected in step (c).

* * * * *

UNITED STATES PATENT AND TRADEMARK OFFICE
CERTIFICATE OF CORRECTION

PATENT NO. : 4,958,529
DATED : September 25, 1990
INVENTOR(S) : Marvin L. Vestal It is certified that error appears in the above-identified patent and that said Letters Patent is hereby corrected as shown below:

In Column 1, line 5, insert:

--Government Support

The invention described herein was made in part during the performance of work under grant number GM 37313 from the Department of Health and Human Services, and the United States Government has a nonexclusive, nontransferable, irrevocable, paid-up license to practice this invention throughout the world.--

In Column 1, line 6, change "continuation" to --continuation-in-part--.

Signed and Sealed this

Seventeenth Day of March, 1992

Attest:

HARRY F. MANBECK, JR.

*Attesting Officer*     Commissioner of Patents and Trademarks